US010098615B2

(12) United States Patent
Gerdes

(10) Patent No.: US 10,098,615 B2
(45) Date of Patent: Oct. 16, 2018

(54) COLLECTING UNIT FOR A STOOL SAMPLE

(71) Applicant: Gerdes Consulting ApS, København Ø (DK)

(72) Inventor: Jens Gerdes, Copenhagen O (DK)

(73) Assignee: Gerdes Consulting ApS, København Ø (DK)

(*) Notice: Subject to any disclaimer, the term of this patent is extended or adjusted under 35 U.S.C. 154(b) by 0 days.

(21) Appl. No.: 14/778,996

(22) PCT Filed: Mar. 24, 2014

(86) PCT No.: PCT/DK2014/000017
§ 371 (c)(1),
(2) Date: Sep. 21, 2015

(87) PCT Pub. No.: WO2014/146665
PCT Pub. Date: Sep. 25, 2014

(65) Prior Publication Data
US 2016/0051234 A1 Feb. 25, 2016

(30) Foreign Application Priority Data

Mar. 22, 2013 (DK) .................................. 2013 00165

(51) Int. Cl.
*A61B 10/00* (2006.01)
*B01L 3/00* (2006.01)

(52) U.S. Cl.
CPC ............ *A61B 10/0038* (2013.01); *B01L 3/50* (2013.01); *B01L 3/502* (2013.01); *B01L 3/508* (2013.01); *B01L 3/5029* (2013.01); *B01L 2300/0867* (2013.01)

(58) Field of Classification Search
CPC ....... A61B 10/0038; B01L 3/50; B01L 3/502; B01L 3/5029; B01L 3/508; B01L 2300/0867
See application file for complete search history.

(56) References Cited

U.S. PATENT DOCUMENTS

| 4,101,279 A * | 7/1978 | Aslam ................ A61B 10/0038 366/314 |
| 5,624,554 A | 4/1997 | Faulkner et al. |
| 6,775,852 B1 | 8/2004 | Alvarez et al. |
| 2001/0044953 A1 | 11/2001 | Gordon |
| 2007/0245486 A1 | 10/2007 | Battle et al. |
| 2012/0316462 A1 | 12/2012 | Enos et al. |

FOREIGN PATENT DOCUMENTS

| JP | H09292392 A | 11/1997 |
| WO | 2009129811 A1 | 10/2009 |

OTHER PUBLICATIONS

International Search Report, PCT/DK2014/000017; dated Jun. 2, 2014 (2 pages).
Supplementary European Search Report, Application No. EP 14770593, dated Nov. 8, 2016, 1 page.

* cited by examiner

*Primary Examiner* — Jill Warden
*Assistant Examiner* — Dwayne K Handy
(74) *Attorney, Agent, or Firm* — Ziegler IP Law Group, LLC

(57) ABSTRACT

The application relates to a unit for collecting a stool sample for medical use. The unit may be used both in the clinic and in the home.

9 Claims, 2 Drawing Sheets

Collection Unit forStool Sample (100)

COLLECTING UNIT FOR A STOOL SAMPLE

SCOPE OF THE APPLICATION

The application relates to a unit for collecting a stool sample for medical use. The unit may be used both in the clinic and in the home.

BACKGROUND

A stool sample may be required to be taken in connection with the diagnosis of diseases in humans and animals.

Stool sampling is normally of great inconvenience to the person who is to collect the sample in terms of odour, hygiene and perception.

A commonly used collection method involves collecting and isolating the stools, which may vary in consistency from liquid to very hard, and transfer with a (sterile) spatula or small scoop to a sample container (for example a container manufactured by Sarstedt, e.g. Sarstedt product number 80.622, product catalogue 2013).

A typical method of isolating the stools is described in the instructions for use for EasySampler® from GP Medical Devices ApS (downloaded from GPMD.dk May 3, 2013). Here the patient defecates on a filtration membrane stretched over the toilet, then transfers the isolated stools to the sample container with the spatula supplied with the sample container.

The quality of the sample is destroyed if all the stools are not kept isolated from contamination with external elements, but is improved if it is "kneaded" or mixed before being transferred to the sample container. This prevents the sample from containing sample material taken only from either the outermost or innermost layer of the stools.

For an effective sample analysis the sample must consist of pure stools, i.e. stools not mixed with anything else, e.g. toilet water or urine.

It also a requirement that the sample container only be partially filled as the stools develop gases when left, leading to explosive redistribution of the stools when the sample container is opened.

These and related problems have been sought solved in the prior art.

WO 2009/129811 for INNOCARE ApS describes a filtration membrane with associated collection unit for a stool sample designed to be fitted on a toilet, more specially between a lavatory bowl and toilet seat, where the collection unit comprises an arrangement for securing the toilet seat, characterised in that the collection unit further comprises an intrinsically funnel-shaped stool feeding element which slopes towards a hole, wherein this collection unit comprises fastening arrangements designed for the temporary retention of a stool sample container for collecting a stool sample through said hole, this fastening arrangement is connected to a section in the periphery of the stool feeding element and is designed to connect the stool feeding element to the toilet.

However, the prior art does not describe solutions which effectively prevent odour nuisance and also prevent urine and other bodily fluids from being collected in the sample container. Moreover, the area surrounding the opening of the sample container comes into contact with the stools during use, resulting in a potential risk of infection for the health care staff. It is also difficult to check that the sample container is not overfilled.

INTRODUCTION

The present invention attempts to overcome the limitations of the prior art.

The object of the invention relates to a collection unit (100) for a stool sample, this collection unit (100) having the form of a container or a bag with a first opening (110), adapted to collect stools, one or more container walls (120), one or more container bottoms (130), and at least two further openings (140, 150) placed in the at least one container wall (120) of the collection unit (100) at a distance from each other, preferably approximately 90° or 180° from each other, wherein the first of the at least two further openings (140) is adapted for temporary fastening of a stool sample container (160), for the purpose of collecting a stool sample through said opening (140), and in that the other of the at least two further openings (150) is adapted for fastening a sample handling unit (170) for the purpose of transferring a stool sample from the one or more container bottom (130) of the collection unit to the stool sample container (160) at the first (140) of the at least two further openings (140, 150).

DESCRIPTION

Figure 1:
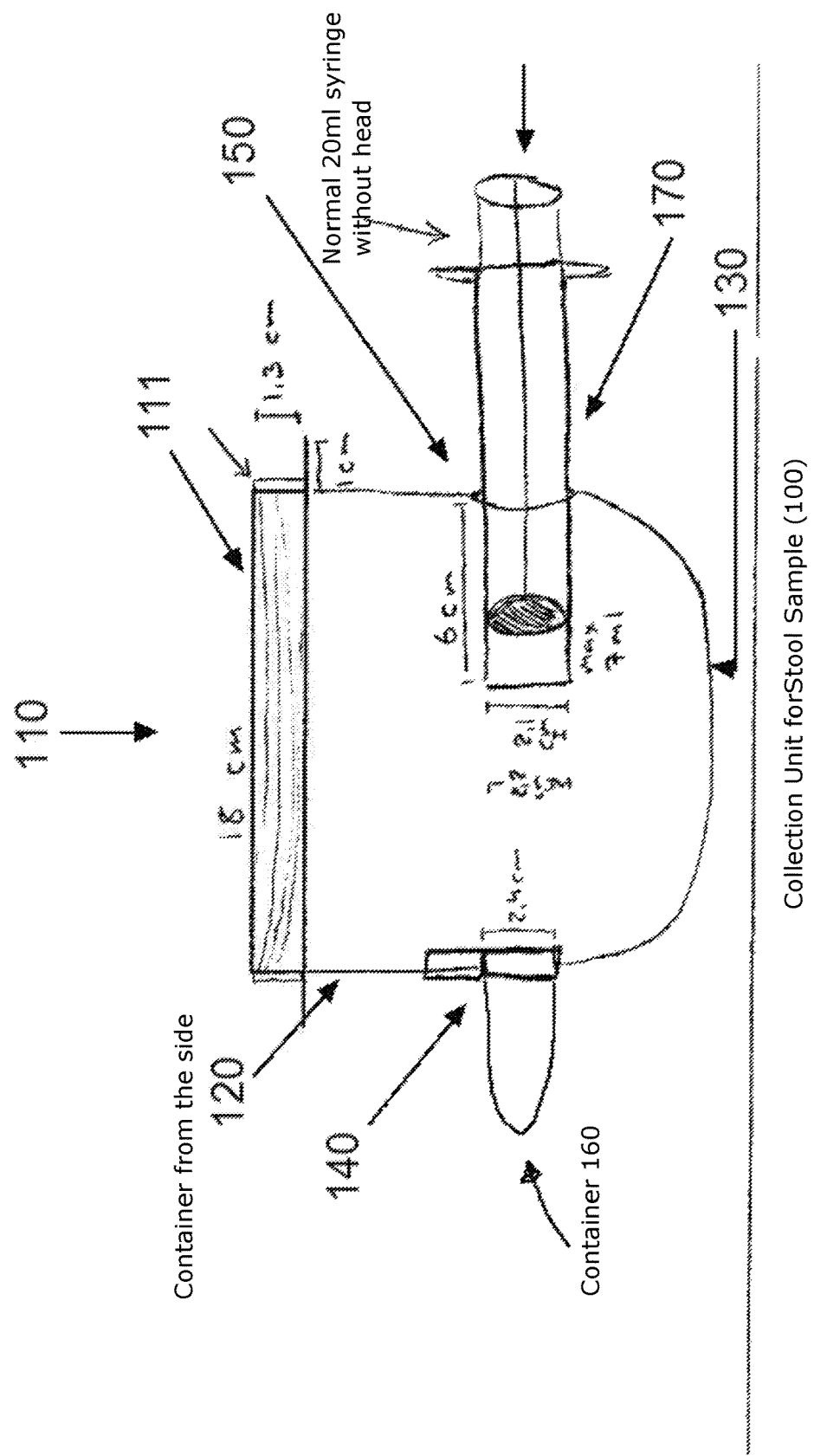
FIG. 1 shows an exemplary embodiment of the collection unit (100) viewed from the side. The figure shows the function of the invention in general terms, with a sample handling unit (170) comprising a piston (171) connected to the collection unit at the opening (150), which enables the piston (171) to be manipulated to push stools towards the opposite opening (140), to which a sample collection container (160, not shown) can be fastened.

The present invention describes a collection unit (100) for collecting a stool sample, wherein the collection unit allows the manipulation of the collected stool sample in such a manner that the sample can easily be isolated from the surrounding environment and reduce direct contact between the stools and the person taking the sample.

Thereby the discomfort is reduced which the person who samples the stool experiences sensorially when handling the sample, thus reducing the risk of spreading infection in certain environments, e.g. at hospitals and among hospital employees, where many stool samples are taken, since the stools are handled inside an almost perfectly sealed container and are therefore almost completely isolated from the surrounding environment.

The object of the invention relates to a collection unit (100) for a stool sample, this sampling unit (100) having the form of a container or bag with a first opening (110) adopted to collect stools, one or more container walls (120), one or more container bottoms (130), and at least two further openings (140, 150), these at least two further openings (140, 150) placed in the at least one container wall (120) of the collection unit (100) at a distance from each other, preferably approximately 90° or 180° from each other, wherein the first of the at least two further openings (140) is adopted for the temporary fastening of a stool sample container (160) for the purpose of collecting a stool sample through said opening (140), and wherein the second of the at least two further openings (150) is adapted for fastening a sample handling unit (170) thereto for the purpose of transferring a stool sample from the container bottom (130) of the collection unit to the stool sample container (160)

temporarily attached to the collection unit (100) at the first (140) of the at least two further openings (140, 150).

FIG. 1 shows an exemplary embodiment of the collection unit (100) viewed from the side. The figure shows the function of the invention in general terms, with a sample handling unit (170) comprising a piston (171) connected to the collection unit at the opening (150), which enables the piston (171) to be manipulated to push stools towards the opposite opening (140), to which a sample collection container (160, not shown) can be fastened.

The person skilled in the art will realize from the description that said one or more container bottoms (130), depending on the choice of material of said one or more container walls (120) of said collection unit (100), may be present during the production of said collection unit (100) or may be formed as a result of the weight of the stools if these deform the container walls, for example when the collection unit is a bag which was initially manufactured without a bottom surface.

It is contemplated that the at least two further openings (140, 150) are fitted apart at a distance of approximately 90° or 180° and at approximately the same height in the side of the at least one container wall (120), but the person skilled in the art will deduce from the description and drawings 1 and 2 that the invention is not limited thereby as the position of the at least two further openings (140, 150) relative to each other is determined solely by the skilled person's choice of method of transferring the stool sample from the collection unit (100) to the sample container (160).

The collection unit (100) will preferably be manufactured from a plastics material, but for sterile reuse, e.g. stainless steel which can be autoclaved, may be preferable.

The collection unit may be fitted with a collar (111). A collar could allow the collection unit to be inserted, for example, into a through hole in a hospital bed pan, where said bed pan is arranged to collect stools and guide the stools down into a pot. The same collar (111) could also be used with a toilet seat designed for this purpose and having a corresponding hole suiting the size of the collar.

For toilet use, however, it will be advantageous for the collar (111) to be provided with a fastening device which allows fastening to the toilet without the use of a specially designed toilet seat. Such fastening devices are well described, for example the person skilled in the art could use a fastening device as described in U.S. Pat. No. 5,412,819, which is incorporated in the present application in its entirety.

To prevent odour nuisance and improve the possibility of isolating the stools from the surrounding environment, the collar (111) may be provided with a device (112) for closing said first opening (110) of the collection unit. This device may, for example, consist of a cord closure or opposing glued surfaces, but the fitting of a lid is also conceivable.

Figure 2:
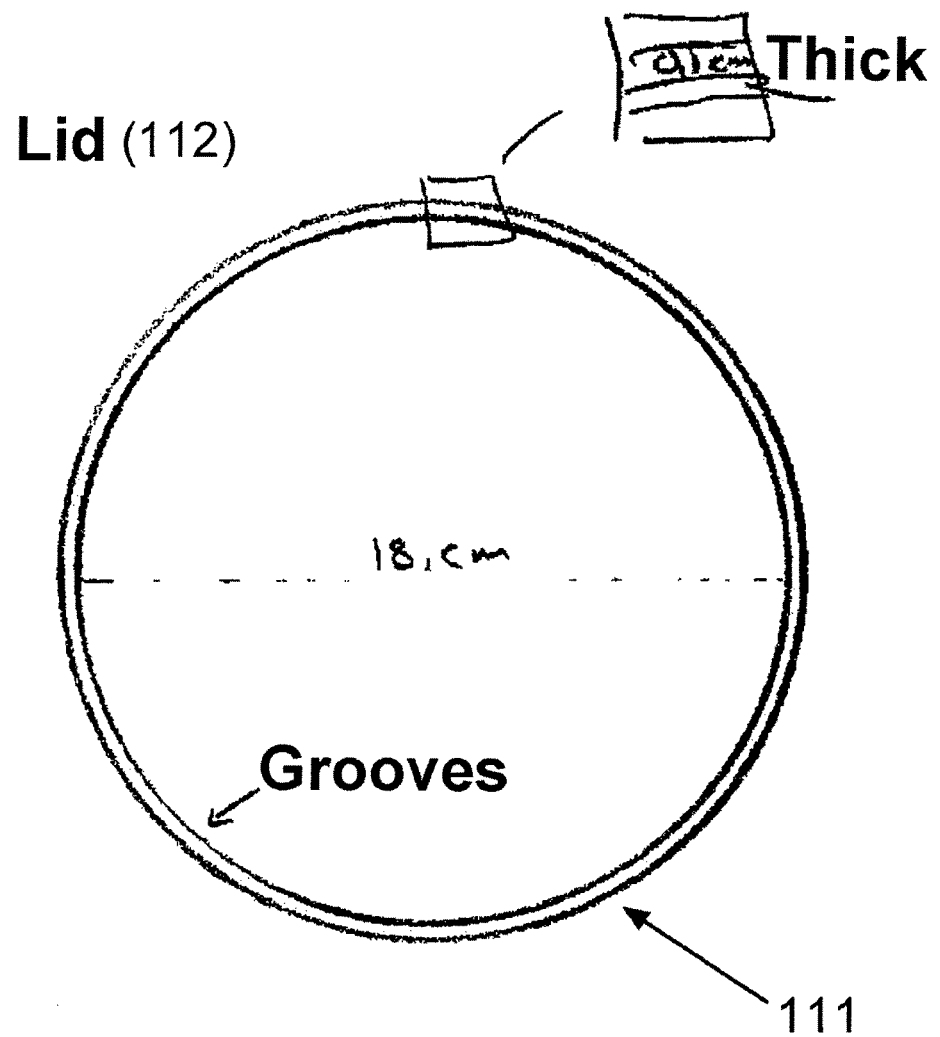
FIG. 2 shows the collection unit (100) viewed from above in, an embodiment where the collection unit is equipped with a collar (111) at the first opening (110) of the collection unit.

FIG. 2 shows the collection unit (100) viewed from above in an embodiment in which the collection unit is equipped with a collar (111) at said first opening (110) of said collection unit. In the embodiment shown the collar is further stiffened so that a lid (112), e.g. a screw lid or a lid in the form of a cover or hood, of plastic for example, can easily be used to close the collection unit (100).

The collection unit (100) may also be fitted with an outer and an inner container or bag, each container or bag preferably having the same shape, wherein the at least two further openings (140, 150) each are throughgoingly mounted and wherein the inner container or bag is perforated, said perforations located in said one or more container bottoms (130) of said internal container or bag. Thereby urine and other bodily fluids accidentally fed into the collection unit can be isolated from the stools without having to open the collection unit (100) to the surrounding area. This enables the stools to be kneaded and improved before sampling without urine and other bodily fluids also being kneaded.

A particularly preferred embodiment of the present invention provides that the sample container (160) is a sample container of the reagent load type, for example such as that manufactured by Sarstedt (e.g. Sarstedt product number 80.622, product catalogue 2013), and the sample handling unit (170) is a small scoop or spatula (172) or a piston (171).

The present invention is not limited to the method whereby the sample container (160) is fastening to the opening (140). For example, some commercial sample containers have screw lids. Such sample containers may therefore be secured in a thread (142) integrated in the opening (140). Other commercial sample containers are smooth at the mouth. Such sample containers may be secured in a tight-fitting gasket (141), for example a rubber gasket.

Correspondingly, the fitting of the sample handling unit (170) may vary according to the design of the unit. For example, if a small scoop or spatula is used, it is sufficient to have an opening, for example the opening (150), through which to insert the spatula, but such openings, like opening (140), may be equipped with a tight-sealing gasket (151), preferably a rubber gasket.

It is generally preferable for the at least two further opening (140, 150) each to be provided with its own gasket (141, 151), preferably a rubber gasket.

Furthermore, the at least two further openings (140, 150) of the collection unit may be provided with remountable seals (145, 155), for example in the form of a seal from self-adhesive plastic or plastic with an adhesive applied to it. This ensures that the collection unit (100) does not leak stools through said at least two further openings (140, 150) after the collection unit has been in use, as well as ensuring that the inside of the collection unit is not contaminated before use.

The invention claimed is:

1. A collection unit (100) for a stool sample the collection unit (100) being in the form of a container or a bag with a first opening (110) arranged to collect stools, a container wall (120) circumscribing the opening (110), and a container bottom (130); at least a second opening (140) and a third opening (150) are extending through the container wall (120) of said collection unit (100), the second opening (140) and the third opening (150) being disposed at a radial distance comprising an angle of approximately 90° or 180° from each other, the second opening (140) being disposed in the container wall (120) at a first height and the third opening (150) being disposed in the container wall (120) at a second height, wherein the first height and the second height are approximately the same; and wherein a stool sample container (160) is detachably attached to the second opening (140) for the purpose of collecting a stool sample through said second opening (140), and wherein a sample handling unit (170) is detachably attached to the third opening (150) for the purpose of transferring the stool sample from the container bottom (130) of the collection unit (120) to said stool sample container (160).

2. A collection unit (100) according to claim 1, having a collar (111).

3. A collection unit (100) according to claim 2, wherein said collar (111) further comprises a device (112) for closing said first opening (110) of said collection unit (100) in the form of a cord closure, opposing glued surfaces or a lid (112).

4. A collection unit (100) according to claim 2, wherein said collar (111) further comprises a fastening device for fastening said collection unit (100) to a toilet seat.

5. A collection unit (100) according to claim 1, having an outer and inner container or bag, wherein the second opening (140) and the third opening (150) are throughgoingly mounted and wherein the inner container or bag is perforated in said one or more container bottoms (130) of said inner container or bag.

6. The collection unit (100) according to claim 1, wherein the collection unit is made of plastic.

7. A collection unit according to claim 1, wherein at least one of the second opening (140) and the third opening (150) are fitted with a gasket (141,151), preferably a rubber gasket.

8. A collection unit according to claim 1, wherein at least one of said second opening (140) and the third opening (150), but preferably both, are provided with remountable seals (145,155), preferably remountable seals of self-adhesive plastics or plastics with adhesive applied to it.

9. The collection unit according to claim 1, wherein the sample handling unit (170) comprises a piston (171) that is configured to push the stool sample towards the second opening (140).

\* \* \* \* \*